United States Patent [19]

Frazer

[11] Patent Number: Plant 6,854

[45] Date of Patent: Jun. 13, 1989

[54] DIEFFENBACHIA HYBRIDA PARADISE

[75] Inventor: Edwin J. Frazer, Brisbane, Australia

[73] Assignee: Hartman Plant Laboratories, Inc., Santa Paula, Calif.

[21] Appl. No.: 23,603

[22] Filed: Mar. 9, 1987

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Hale and Dorr

[57] ABSTRACT

A new and distinct cultivar of Dieffenbachia known as Dieffenbachia Hybrida Paradise which is a seedling cross between Marianne and Wilson's Delight.

1 Drawing Sheet

The invention comprises a new and distinct cultivar of Dieffenbachia known as Dieffenbachia Hybrida Paradise.

The new cultivar is a product of a seedling cross between Dieffenbachia Marianne and Wilson's Delight.

The following observations, measurements and values describe plants grown in Alva, Fla. under greenhouse conditions that closely approximate those generally used in horticultural practice. All color references are measured against The Royal Horticultural Society colour chart. Colors are approximate as color depends on horticultural practices such as light level and fertilization rate among others.

The following traits have been repeatedly observed to be characteristics which in combination distinguish Dieffenbachia Paradise from other commercially available Dieffenbachia.

Distinctions

1. The leaf is oval compared to other commercial Dieffenbachia.
2. The midrib is white on both sides of the leaf.
3. The leaf is completely patterned with green and yellow blotches fading to white with age oriented in long files about 45° relative to the midrib.
4. The leaves are held relatively upright so both sides can be seen.
5. The surface of the leaf is not deeply ribbed but is fairly flat with thin closely spaced (1 mm) sunken, secondary veins going from the midrib and merging at the leaf margin.
6. The leaf is very thick but flexible.
7. The breaks produce large leaves quickly.
8. The leaf tip is cupped slightly.

The appearance and distinctive character of Paradise is shown in the FIGURE which is a true color photograph of the cultivar in an eight-inch pot.

DESCRIPTION

Propagation: Asexual production either through tissue culture or division.

Plant: In a 6 inch pot, Paradise will be approximately 20 cm to 24 cm from the soil surface to the junction of the petioles of the last two unrolled leaves and approximately 38 cm to 40 cm in width after approximately 26 weeks to 36 weeks under appropriate growing conditions from tissue culture. All measurements are based on the above parameters.

Stem:

*Growth pattern.*—The stem is erect in growth and will be approximately 2.2 cm to 2.4 cm in diameter at a height of 5 cm above the soil surface. Internode distance will be approximately 1.4 cm to 1.8 cm at a height of 3 cm above the soil.

*Color.*—The stem is green with gray green blotches.

Petiole (based on the fourth expanded leaf from apex of the dominant shoot):

*Pattern.*—The petiole has fleshy edges extending from the midrib that will be referred to as wings. The wings will be approximately 7 mm to 9 mm wide 1 cm below the leaf base. The wings extend from the base of the petiole to within approximately 0.1 cm to 0.3 cm of the leaf base on upper leaves and approximately 1.2 cm to 1.8 cm on lower leaves. The apex of the wings is emarginate. The petiole follows the stem axis but diverges from the axis approximately 3.5 cm to 4.5 cm from the leaf base forming a horizontal distance from the edge of the stem to the leaf base of approximately 1.5 cm to 2.0 cm.

*Physical dimensions.*—The petiole will be approximately 8.4 to 9.0 cm from its base to the base of the leaf. The petiole will be approximately 6 mm to 8 mm in diameter one half way between the top of the wing to the bottom of the leaf.

*Color and color pattern.*—The petiole wings will be green and the midrib will be greenish white.

Leaf:

*Growth pattern.*—The leaf will be orbicular with an aristate/cuspidate apex and a cordate base. The margin is entire. The leaf is asymmetric with the side of the leaf unrolling first having less surface area and less undulations on the leaf margin than the side unrolling last. The leaf is oriented 5° to the stem axis at the time of full unrolling changing to 60° to the stem axis as more leaves unroll above it. The midrib is slightly drooped over the length of the leaf. The leaf blade is flat from the midrib to the margin.

*Physical dimensions.*—For the potsize and growing time indicated, the largest leaf will be approximately 20 cm to 23 cm long and approximately 12.5 cm to 14.0 cm wide. An average sized leaf will be approximately 18 cm to 21 cm long and approximately 11 cm to 13 cm wide. The leaf thickness is medium.

*Midrib.*—The midrib is thick and is white with green at the base of the leaf.

*Primary veins.*—The primary veins are sunken into the adaxial side and protruding out of the abaxial side.

*Color and pattern.*—The adaxial surface of the mature, older leaf has a midrib color of 145 at the junction with the petiole, abruptly changing to 157A immediately above, and a leaf blade background and blotch of color of 157B and 144A with leaf edge and irregular leaf blade areas of 139A. The abaxial surface of the mature, older leaf has a midrib color opf 155A, with main veins of 155A changing to 137A as they approach the leaf edge; the leaf blade background color is 137A, blotched with 137D. The adaxial surface of the newly-opened leaf has a midrib color of 155C and a leaf blade background color of 139A with blotches of 1C, 1D radiating from the midrib. The abaxial surface of the newly-opened leaf has a midrib of 155A, with main veins of 155A, changing to 137C as they approach the leaf edge, and a leaf blade background color of 137C, blotched with small areas of 145B.

*Texture.*—The leaf is slightly rigged and very reticulate on the adaxial side and smooth on the abaxial side.

Axillary breaks: There will be approximately 5 to 7 axillary breaks with at least 1 leaf expanded. Leaves will show color by the second leaf and will have true color and pattern by the third leaf.

Inflorescences: not present.

Roots: Thick white roots with finer laterals.

General observations: Dieffenbachia Paradise is unique in the shape of the leaf and the coloration pattern. The leaves are upright and have white veins on both sides giving good color throughout the plant and a very dense appearance. The variegation is arranged in files giving the appearance of stripes. The leaves are thick and very stiff. The breaks develop large leaves quickly making the base of the plant fairly full. The plant has an overall yellow green appearance.

I claim:

1. A new and distinct cultivar of Dieffenbachia as described and illustrated.

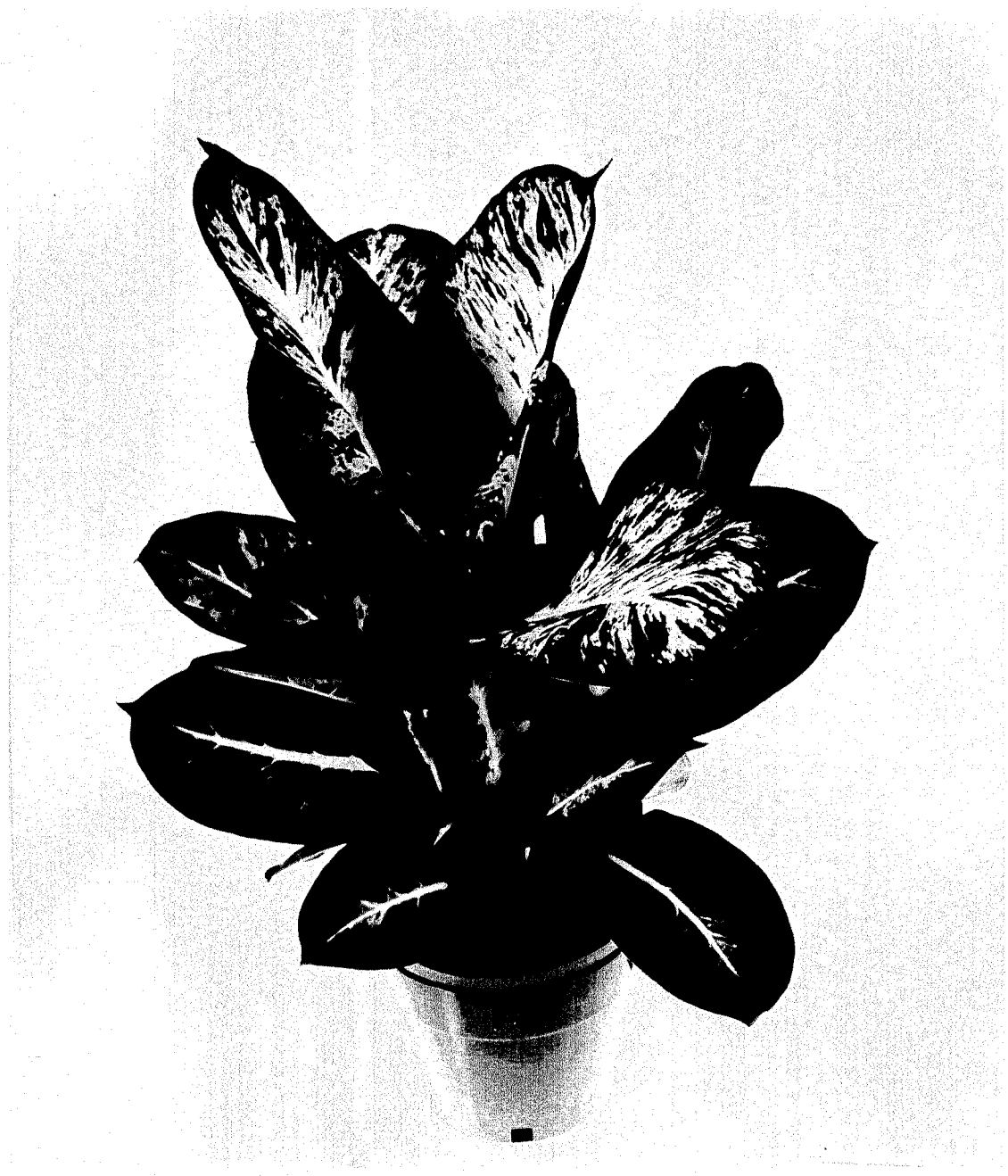

* * * * *